(12) United States Patent
Maruyama et al.

(10) Patent No.: US 9,737,423 B2
(45) Date of Patent: Aug. 22, 2017

(54) STENT WITH DRUG COAT LAYER

(71) Applicant: TERUMO KABUSHIKI KAISHA, Shibuya-ku, Tokyo (JP)

(72) Inventors: Kazuhiro Maruyama, Kanagawa (JP); Noboru Saito, Kanagawa (JP); Hiroki Goto, Kanagawa (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 0 days.

(21) Appl. No.: 14/733,707

(22) Filed: Jun. 8, 2015

(65) Prior Publication Data
US 2015/0265440 A1   Sep. 24, 2015

Related U.S. Application Data

(60) Division of application No. 13/413,372, filed on Mar. 6, 2012, now Pat. No. 9,095,459, which is a
(Continued)

(30) Foreign Application Priority Data

Sep. 30, 2009   (JP) .................................. 2009-227417

(51) Int. Cl.
*A61F 2/06* (2013.01)
*A61F 2/89* (2013.01)
(Continued)

(52) U.S. Cl.
CPC ................ *A61F 2/89* (2013.01); *A61F 2/915* (2013.01); *A61L 31/10* (2013.01); *A61L 31/16* (2013.01);
(Continued)

(58) Field of Classification Search
CPC ......................................................... A61F 2/82
(Continued)

(56) References Cited

U.S. PATENT DOCUMENTS 5,282,823 A     2/1994  Schwartz et al.
5,824,049 A  * 10/1998  Ragheb .................... A61F 2/82
                                                                  604/265
(Continued)

FOREIGN PATENT DOCUMENTS

CN        201006050 Y    1/2008
EP        0 800 801 A1   10/1997
(Continued)

OTHER PUBLICATIONS

Office Action (Patent Examination Report No. 2) issued on Jul. 17, 2015, by the Australian Patent Office in corresponding Australian Patent Application No. 2010301898. (3 pages).
(Continued)

*Primary Examiner* — Jacqueline Woznicki
(74) *Attorney, Agent, or Firm* — Buchanan, Ingersoll & Rooney PC

(57) ABSTRACT

A stent able to minimize occurrences of strain and stress concentration in a drug coat layer upon expansive deformation of the stent in a radial direction to avoid the possibility of the drug separating from the stent, includes a stent body and a drug coating layer coated on the outside surface of the stent body so that the thickness of the drug coating layer gradually decreases toward a bent portion of the stent.

9 Claims, 10 Drawing Sheets

Related U.S. Application Data continuation-in-part of application No. PCT/JP2010/065740, filed on Sep. 13, 2010.

(51) Int. Cl.

| | | |
|---|---|---|
| *A61L 31/10* | (2006.01) | |
| *A61L 31/16* | (2006.01) | |
| *A61F 2/915* | (2013.01) | |
| *A61L 27/54* | (2006.01) | |
| *A61L 27/40* | (2006.01) | |
| *A61F 2/82* | (2013.01) | |
| *B05B 13/02* | (2006.01) | |

(52) U.S. Cl.
CPC . *A61F 2/06* (2013.01); *A61F 2/82* (2013.01); *A61F 2002/9155* (2013.01); *A61F 2002/91516* (2013.01); *A61F 2002/91558* (2013.01); *A61F 2002/91575* (2013.01); *A61F 2002/91583* (2013.01); *A61F 2210/0076* (2013.01); *A61F 2230/0006* (2013.01); *A61F 2230/0069* (2013.01); *A61F 2240/001* (2013.01); *A61F 2250/003* (2013.01); *A61F 2250/0026* (2013.01); *A61F 2250/0029* (2013.01); *A61F 2250/0031* (2013.01); *A61F 2250/0036* (2013.01); *A61F 2250/0037* (2013.01); *A61F 2250/0041* (2013.01); *A61F 2250/0067* (2013.01); *A61F 2310/00017* (2013.01); *A61F 2310/00023* (2013.01); *A61F 2310/00035* (2013.01); *A61F 2310/00059* (2013.01); *A61F 2310/0097* (2013.01); *A61F 2310/00149* (2013.01); *A61F 2310/00155* (2013.01); *A61F 2310/00389* (2013.01); *A61L 27/40* (2013.01); *A61L 27/54* (2013.01); *A61L 2300/00* (2013.01); *A61L 2420/08* (2013.01); *B05B 13/0235* (2013.01)

(58) Field of Classification Search
USPC ...................................................... 623/1.42
See application file for complete search history.

(56) References Cited

U.S. PATENT DOCUMENTS

| | | | |
|---|---|---|---|
| 6,027,526 A | 2/2000 | Limon et al. | |
| 6,395,326 B1 | 5/2002 | Castro et al. | |
| 6,805,898 B1 | 10/2004 | Wu et al. | |
| 6,979,346 B1 | 12/2005 | Hossainy et al. | |
| 7,014,654 B2 | 3/2006 | Welsh et al. | |
| 7,335,314 B2 | 2/2008 | Wu et al. | |
| 7,628,807 B2 | 12/2009 | Flanagan | |
| 7,951,392 B2 * | 5/2011 | Boulais | A61L 31/10 424/422 |
| 8,523,938 B2 * | 9/2013 | Takeuchi | A61F 2/91 427/256 |
| 8,864,820 B2 * | 10/2014 | Foreman | A61L 31/10 623/1.46 |
| 2002/0038145 A1 | 3/2002 | Jang | |
| 2003/0028242 A1 | 2/2003 | Vallana et al. | |
| 2003/0088307 A1 | 5/2003 | Shulze et al. | |
| 2003/0149479 A1* | 8/2003 | Snyder | A61F 2/147 623/6.16 |
| 2004/0039437 A1* | 2/2004 | Sparer | A61L 27/34 623/1.15 |
| 2005/0015142 A1 | 1/2005 | Austin et al. | |
| 2005/0038505 A1 | 2/2005 | Shulze et al. | |
| 2006/0095123 A1 | 5/2006 | Flanagan | |
| 2006/0212109 A1 | 9/2006 | Sirhan et al. | |
| 2008/0033536 A1 | 2/2008 | Wittchow | |
| 2009/0264975 A1 | 10/2009 | Flanagan et al. | |
| 2010/0034960 A1 | 2/2010 | Kindaichi et al. | |
| 2011/0202122 A1 | 8/2011 | Takeuchi et al. | |

FOREIGN PATENT DOCUMENTS

| | | |
|---|---|---|
| EP | 1 277 449 A1 | 1/2003 |
| JP | 9-285548 A | 11/1997 |
| JP | 2003/0088307 A1 | 5/2003 |
| JP | 2004-528928 A | 9/2004 |
| JP | 2005/508671 A | 4/2005 |
| WO | WO 03/009779 A2 | 2/2003 |
| WO | WO 2008/024712 A2 | 2/2008 |
| WO | WO 2008/114585 A1 | 9/2008 |

OTHER PUBLICATIONS

International Search Report (PCT/ISA/210) issued on Nov. 30, 2010, by Japanese Patent Office as the International Searching Authority for International Application No. PCT/JP2010/065740.

Extended European Search Report dated Oct. 31, 2012, issued by the European Patent Office in corresponding European Patent Application No. 10820337.3 (6 pages).

Office Action (Notification of First Office Action) issued on Dec. 30, 2013, by the Chinese Patent Office in corresponding Chinese Patent Application No. 201080023374.5 and an English translation of the Office Action. (16 pages).

Australian Patent Examination Report No. 1 dated Oct. 31, 2014 for corresponding Application No. 2010301898.

European Office Action "Communication pursuant to Article 94(3) EPC" mailed May 23, 2016 in counterpart European Application No. 10820337.3 (6 pages, in English).

Canadian Office Action mailed Feb. 18, 2016 in counterpart Canadian Application No. 2,767,994 (3 pages, in English).

Korean Official Action ("Notice of Preliminary Rejection") mailed Aug. 5, 2016 in the counterpart Korean Application No. 10-2012-7004325 with complete English translation (7 pages).

Office Action (Examination Report No. 1 for Standard Patent Application) issued on Dec. 20, 2016 by the Australian Patent Office in corresponding Australian Patent Application No. 2015261573. (3 pages).

* cited by examiner

STENT WITH DRUG COAT LAYER

The present application is a continuation of U.S. Ser. No. 13/413,372, filed Mar. 6, 2012, which is a continuation-in-part of International Application No. PCT/JP2010/065740 filed on Sep. 13, 2010, and claims priority to Japanese Patent Application No. 2009-227417 filed on Sep. 30, 2009, the entire content of all of which is incorporated herein by reference.

TECHNICAL FIELD

The present invention relates to a stent which is indwelled at a stenosed region or an occluded region in a lumen of an organism so that a patency state of the lumen is maintained. More particularly, the invention involves a drug eluting type stent called DES (Drug Eluting Stent) in which drug is coated on the outside surface of a stent body.

BACKGROUND DISCUSSION

A stent is a medical device used for improving a stenosed region or an occluded region in a lumen in an organism such as a blood vessel, a bile duct, a trachea, an esophagus, an urethra or the like. Generally speaking, the stent is a network-like cylindrical body formed by successively forming, using a thin strut, a straight or curved linear portion or a bent portion of a U shape or the like on the same plane, so to speak, into a wavy form and disposing a plurality of wavy annular bodies, in each of which such wavy struts are disposed annularly and connected to each other, in an aligned relationship with each other in an axial direction.

While a stent is used, for example, in a coronary artery of the heart, for restenosis prevention after the percutaneous transluminal coronary angioplasty (PTCA), it is recognized that, if a stent on which drug is not coated (i.e., a bare metal stent) is used such that the stent is reduced in size in advance and reaches a target region, in which it is expanded so as to be indwelled in a lumen, although the restenosis rate is low in comparison with a case where only PTCA is used without using a stent at all, restenosis occurs at a ratio of approximately 20 to 30% in the stent indwelling region. Principal causes of the restenosis are intimal hypertrophy by migration and growth of vascular smooth muscle cells.

Accordingly, development of a DES is carried out recently in which a drug capable of suppressing migration and growth of vascular smooth muscle cells is coated on the outer surface of a stent (referred to sometime as "stent body") such that the drug is eluted in a stent indwelling region to prevent restenosis. For example, the drug used include sirolimus and carcinostatic. The coating of the drug is carried out such that a coating liquid including a drug and a biocompatible polymer which are dissolved in solvent is coated by a dipping method, a spray method, or a direct application method (applying drug along a strut which configures a stent body) or the like so that a predetermined amount of drug exists on the surface of the stent body and then the coating liquid is dried and solidified.

However, in order to cause the DES to be indwelled in a lumen, after the stent reaches a target region in a lumen in a state in which the stent is reduced in diameter once, the stent is expanded and put so as to be indwelled. It has been found that a problem occurs in that the drug coat layer coated on a bent portion or the like is exfoliated from the surface of the stent body following the expansion and deformation of the stent (particularly in the bent portion) and the drug itself is destroyed and comes off from the stent body. This problem is particularly acute where the drug coat layer exhibits brittleness.

International Application Publication No. WO 03/009779A2 discloses forming a drug coat layer in the form of a line or in the form of a dot in a region other than a bent portion ("stress region" or "mechanical profile") of the stent or form a drug coat layer in the form of a dot at a bent portion.

However, there is the possibility that, in a stent in which a drug coat layer is formed in the form of a dot, the amount of the drug may be insufficient, and this is not preferable. Further, even in a stent in which a drug coat layer is formed in the form of a line at a portion other than the curved portion, there is the possibility that a start point of deformation by expansion may coincide with an end portion of the drug coat layer or, depending upon a case, a start point of deformation may exist in a portion in which the drug coat layer is formed. Therefore, there is the possibility that strain or stress concentration may occur in the drug coat layer and the drug may be exfoliated from the surface of the stent body and then the exfoliation may propagate further to destroy the drug coat layer and cause removal of a significant amount of the drug coat layer. In particular, where the stent is expanded in a radial direction, the magnitude or the like of expansion is not constant and is different for each procedure, and coating of the drug is carried out for a bent portion to be expanded without taking which position becomes a start point of deformation into consideration. Therefore, even if coating is carried out uniformly except at a bent portion, if a start point of deformation and an end portion of the drug coat layer coincide with each other, then strain or stress concentration occurs in the drug coat layer and exfoliation, destruction and coming off of the drug occurs.

SUMMARY

The stent disclosed here is constructed so that the thickness of a drug coat layer coated on the outside surface of a stent body gradually decreases toward a bent portion so that the occurrence of strain or stress concentration in the drug coat layer upon deformation by expansion of the stent is reduced greatly and the drug coat layer itself can be relatively easily deformed in accordance with deformation of the stent. This helps prevent the drug from separating from the stent.

The gradually decreasing portion of the drug coat layer at which the thickness of the drug coat layer is gradually decreased toward the bent portion is beneficial in that even if a start point of the deformation by expansion of the stent shifts a little from the bent portion of the strut, the drug coat layer at the start point of the deformation and the proximity of the start point is thinner. Accordingly, the occurrence of strain or stress concentration in the drug coat layer is reduced greatly, and separation or coming off of the drug can be prevented.

The application amount of the drug is relatively small at the gradually decreasing portion and so the drug itself is better able to follow-up deformation of the stent. Also in this regard, coming off or separation of the drug can be prevented.

Because the stent is configured such that the separation of the drug from the stent, or the coming off of the drug, can be prevented without using an additive such as a plasticizer, bad influence on an organism is not likely to occur and the safety of the stent is quite high.

A predetermined range or region around the start point (a bent point) of deformation by expansion of the bent portion is preferably configured as a no-coat layer. Therefore, the drug is not coated in a region in which the occurrence of strain or stress concentration is most likely to appear. Therefore, the stent is able to suppress the separation or coming off of the drug and can cope rather readily with various expansion states in an indwelled region thereof, and is relatively easy to handle, relatively easy and certain to procedure and very good in convenience of use.

The thin film coat layer of the drug preferably extends within a predetermined region or range around a bent point (inflection point) of the bent portion and so the drug can be readily secured quantitatively while coming off or separation of the drug is suppressed.

The drug coat layer is preferably formed from a mixture of the drug and a polymer, and so the coating process for the outer surface of the strut can be carried out readily, and also the workability is improved.

The polymer is preferably a biodegradable polymer such as, for example, polylactic acid, polyglycolic acid, a lactic acid-glycolic acid copolymer or a lactic acid-ϵ-caprolactone copolymer. Therefore, after the stent is indwelled in an organism, the polymer which covers and protects the drug is biodegraded and the drug is released, and consequently, restenosis in the stent indwelled region can be prevented with relative certainty.

A primer coat layer is preferably provided between the stent body and the drug coat layer. This thus provides good bonding between the stent body and the drug, and relatively low exfoliation possibility.

The inclination angle of the gradually decreasing portion is preferably 1 to 45 degrees. When the stent is deformed by expansion, strain or stress concentration is thus less likely to occur in the drug coat layer, and this stent can be formed or produced rather readily.

The stent body is preferably formed in a cylindrical shape by disposing and joining together a plurality of wavy annular bodies, each of which is formed from a wavy strut having a bent portion, in an aligned relationship with each other in an axial direction. Therefore, a stent of a predetermined length can be obtained by connecting the wavy annular bodies, and not only production of the stent body but also production of a DES are facilitated.

The drug coat layer is preferably formed as a plurality of thin film coat layers produced by discharging coating liquid from a nozzle and moving the nozzle along the strut so that the coating length of the thin film coat layer of an upper layer is set shorter than the coating length of the thin film coat layer of a lower layer so that the gradually decreasing portion is formed in a stairway shape. Therefore, the gradually decreasing portion can be formed readily.

Upon forming the gradually decreasing portion as described above, the nozzle is moved from one of such struts toward the other strut at the bent portion. Therefore, the gradually decreasing portion can be formed or produced rapidly.

The drug coat layer is preferably formed using a spray or an inkjet, and this allows the formation of the drug coat layer to be carried out readily and rapidly. Particularly where an inkjet is used for the formation, relatively little loss of the drug occurs, and the drug coat layer can be formed with a relatively high degree of accuracy.

Another aspect of the disclosure here involves a stent positionable in a body lumen and radially inwardly contracted to permit placement of the stent in a body lumen and radially outwardly expanded after placement in the body lumen to secure an opening in the body lumen. The stent includes a cylindrical stent body comprised of a plurality of annular wavy bodies each comprised of a wave-shaped strut configured to include plural bent portions and plural connecting portions, with each connecting portion connecting pairs of the bent portions, the bent portions each possessing an inflection point, the bent portions being subjected to deformation when the stent is contracted and expanded. The plurality of annular wavy bodies are axially arranged, with axially adjacent ones of the annular bodies connected by a joint portion. The stent further includes a drug coat layer on an outer surface of the struts forming at least some of said annular wavy bodies. The drug coat layer includes a plurality of spaced apart drug coat layer thickness reducing regions at which the drug coat layer on the outer surface of the struts possessing a thickness that gradually decreases, the drug coat layer thickness reducing regions being located at parts of the struts on opposite sides of the inflection points of the bent portions.

An additional aspect of the disclosure here involves a method of applying a drug coat layer to a stent. The method involves applying a drug coat layer to a wave-shaped strut of a stent, wherein the wave-shaped stent includes a plurality of bent portions and a plurality of connecting portions, with each connecting portion connecting two of the bent portions, and the wave-shaped strut possessing an annular-shape to form an annular wavy body, and with the annular wavy body being one of a plurality of axially arranged interconnected annular wavy bodies which together form the stent. The applying of the drug coat layer involves applying the drug coat layer to the wavy-shaped strut so that a thickness of the drug coat layer in regions of the stent approaching the bent portions is gradually reduced.

DETAILED DESCRIPTION

Figure 1:
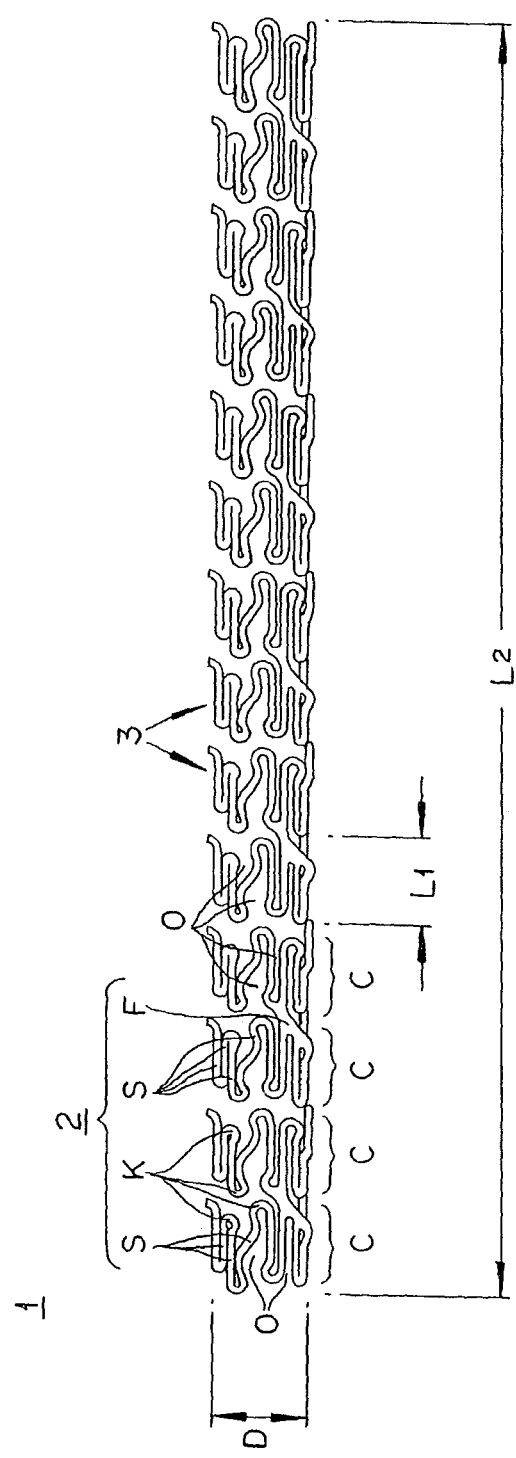
FIG. 1 is a schematic front view of an embodiment of the stent disclosed here.

Referring initially to FIG. 1, the stent disclosed here generally includes a cylindrical stent body 2 formed from thin struts 3 and having, so to speak, a reticulated state or construction, and a drug coat layer 4 (refer to FIGS. 6A and 6B) coated on the surface of the stent body 2.

Figure 2:
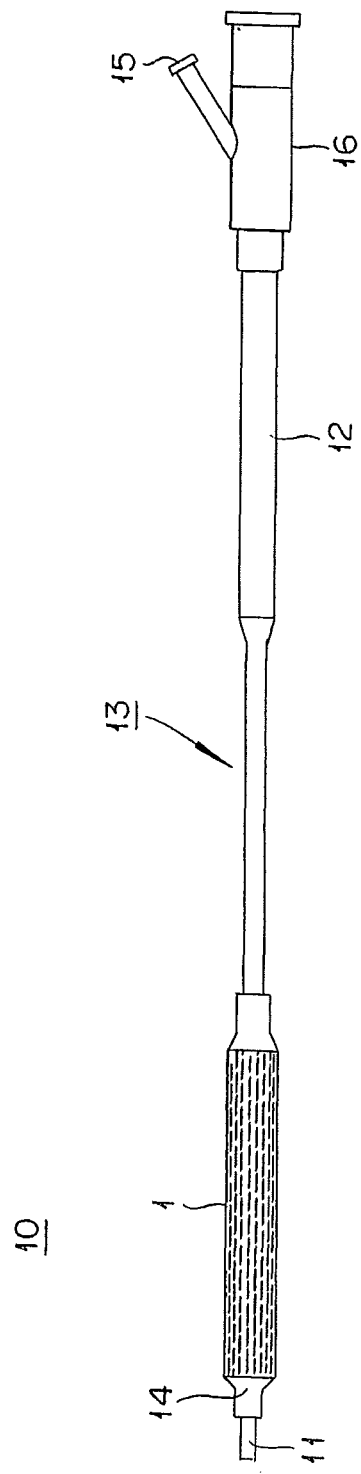
FIG. 2 is a schematic front view of the stent depicted in FIG. 1 in a used state.

The stent 1 is indwelled into the inside of a blood vessel or the like by using, for example, a stent delivery system such as the one shown by way of example in FIG. 2. The stent delivery system 10 is configured from a shaft body 13 of a double tube structure formed from an inner tube 11 and an outer tube 12 disposed coaxially with each other, a foldable and expandable balloon 14 at a distal end portion of the shaft body 13, and a branch hub 16 having an injection port 15 for injecting fluid for balloon expansion.

In order to indwell the stent 1 into a blood vessel by using this stent delivery system 10, the stent 1 is first reduced in diameter and mounted on the stent delivery system 10 in such a manner as to enclose the balloon 14 in a folded state. A guide wire is fitted into the inside of the inner tube 11 which is open at the distal end thereof, and the stent delivery system 10 on which the stent 1 is mounted is then guided to a predetermined position in the blood vessel by using the guide wire as a guide. Then, fluid is injected from the injection port 15 so that it flows into the balloon 14 through a lumen between the inner tube 11 and the outer tube 12 to expand the balloon 14. When the stent 1 attached to the balloon 14 is expanded outwardly in a radial direction from the inside, the stent 1 is extended and plastically deformed in the radial direction and/or an axial direction, and is allowed to indwell in the expanded state in the blood vessel.

Figure 3:
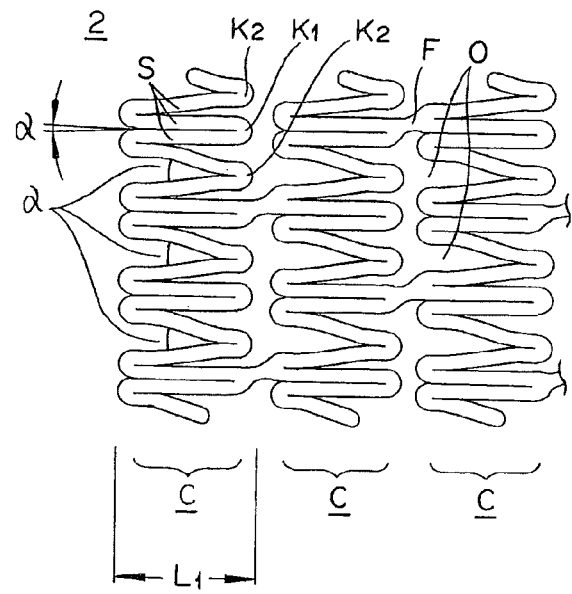
FIG. 3 is an enlarged plan view of the stent depicted in FIG. 1 in a state in which it is reduced in diameter.

Set forth below is a more detailed description of features and aspects of the stent 1 disclosed here. The stent body 2 of this embodiment disclosed by way of example includes, as shown in FIGS. 1 and 3, a circumferentially alternating arrangement of a bent portion K1 which is U-shaped and has a relatively small opening angle α, a bent portion K2 which is V-shaped and has a relatively large opening angle α, and a linear portion S which is a straight portion or a curved portion. The linear portions S are examples of connecting portions connecting the bent portions. These portions K1, K2, S are circumferentially arranged in an annular shape to form a wavy annular body C (also referred to as "cell part C"). The length of each cell part C in the axial direction is "L1." A distal end of the U-shaped bent portion K1 in one cell part C and a proximal end of the U-shaped bent portion K1 of the U-shape in an axially adjacent cell part C are joined together successively at a joint portion F to generally form a cylindrical body, so to speak, in a reticulated state, wherein a plurality of cell parts C are connected to each other and the length of which in the axis direction is "L2." The stent body 2 shown in FIG. 1 is configured from fourteen (14) cell parts C.

Figure 4:
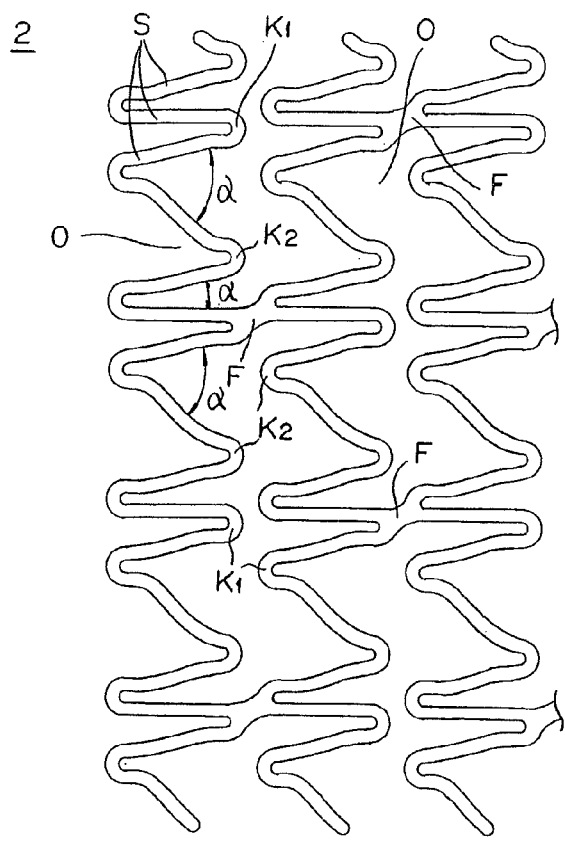
FIG. 4 is an enlarged plan view of the stent depicted in FIG. 1 in an expanded state.

When the stent body 2 is enlarged in a radial outward direction from a contracted state shown in FIG. 3, it is changed into an expanded state wherein the opening angles α increase as shown in FIG. 4 and portions of the wave-shaped struts 3 which configure the bent portion K1 or the bent portion K2 are spaced away from each other such that an gap portion O is enlarged or widened.

The bent portions K1 and K2 of the stent body 2 are preferably configured so that the bent portion is bent not at an acute angle, but is bent or curved in a U shape or in a gently arcuate shape. This configuration helps reduce the occurrences of strain applied to the drug coat layer 4, hereinafter described, upon expansion of the stent. The effect of suppressing exfoliation, damage, destruction or coming off of the drug coat layer 4 is thus quite high. However, the curved structure of the bent end portion is preferably curved to such a degree that it does not swell by a great amount toward an outer direction, that is, to such a degree that the bent end portion does not swell outwardly in an arc. Since the bent end portion is shaped in this manner, the outer diameter upon contraction in diameter can be reduced, and also insertion into an in vivo organism (for example, a blood vessel) of a small diameter is facilitated.

As the material for forming the stent body 2, preferably a material having biocompatibility is used. Examples of preferable materials include stainless steel, tantalum or tantalum alloy, platinum or platinum alloy, gold or gold alloy, cobalt-based alloy, cobalt chromium alloy, titanium alloy, and niobium alloy. As stainless steel, SUS316L having the highest corrosion resistance is most preferable.

In the stent body 2, the area occupied by the strut 3 in a state in which it is mounted on the balloon 14 preferably is 60% to 80% of the area of the entire outer peripheral face including the gap portions O.

The width of the wave-shaped strut 3 preferably is 40 μm to 150 μm, and particularly preferably is 80 μm to 120 μm. The length L1 of each cell part C in the axial direction preferably is 0.5 mm to 2.0 mm, and particularly preferably is 0.9 mm to 1.5 mm. The diameter D1 of the stent body 2 upon non-expansion preferably is 0.8 mm to 2.5 mm, and more particularly is 0.9 mm to 2.0 mm. The length L2 upon non-expansion preferably is approximately 8 mm to 40 mm.

Formation of the stent body 2 is carried out by removing portions from a tube body (particularly a metal pipe) other than the struts to form a predetermined pattern. For example, the formation is carried out by removing the gap portions O from a metal pipe by an etching method which utilizes masking called photo fabrication and a chemical, an electrical discharge machining method based on a mold, a cutting method (for example, mechanical grinding, laser cutting) or the like.

After such formation, an edge of the struts 3 is removed by chemical polishing or electrolytic polishing to finish the struts 3 so that they have a relatively smooth face.

Further, after the formation into a predetermined pattern, annealing may be carried out. The annealing improves the plasticity and flexibility of the overall stent, the indwelling property in a bent blood vessel and reduces physical stimuli to be applied to the inner wall of the blood vessel, and can reduce main causes of restenosis. The annealing is preferably carried out such that the stent is cooled slowly after it is heated to 900° C. to 1200° C. under an inert gas environment (for example, mixed gas of nitrogen and hydrogen) so that an oxide film may not be formed on the surface of the stent.

Although various methods such as, for example, a dipping method, a spray method, an ink jet method and a nozzle jet method can be used for the formation of the drug coat layer 4, in the stent disclosed here by way of example, a spray method, an ink jet method and a nozzle jet method are preferable.

Here, the spray method generally involves jetting drug to the outside surface of the stent body 2 together with an air flow to form the drug coat layer 4. The ink jet method generally involves applying drug in the form of fine particles to the outside surface of the stent body 2. Further, the nozzle jet method generally involves applying drug to the outside surface of the stent body 2 from a nozzle.

When the spray method or the ink jet method is used, formation of the drug coat layer can be carried out relatively readily and rapidly. When the ink jet method or the nozzle jet method is used, the loss of the drug is rather small little and a drug coat layer can be formed with a relatively high degree of accuracy.

Figure 5:
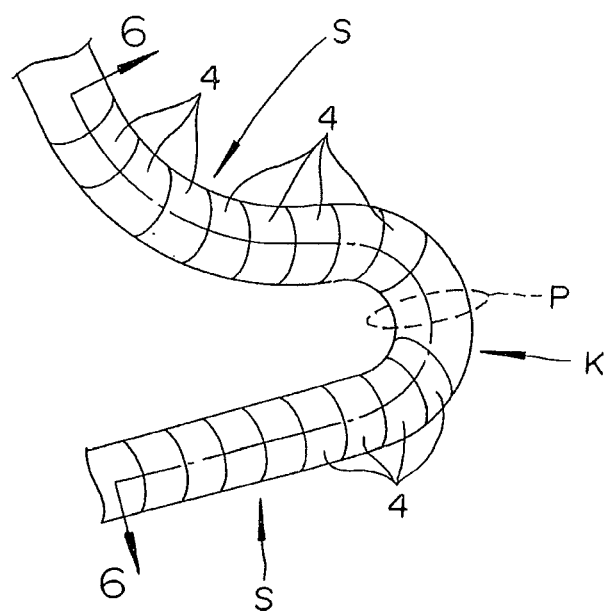
FIG. 5 is an enlarged plan view of a bent portion of the stent depicted in FIG. 1.
Figure 6A:
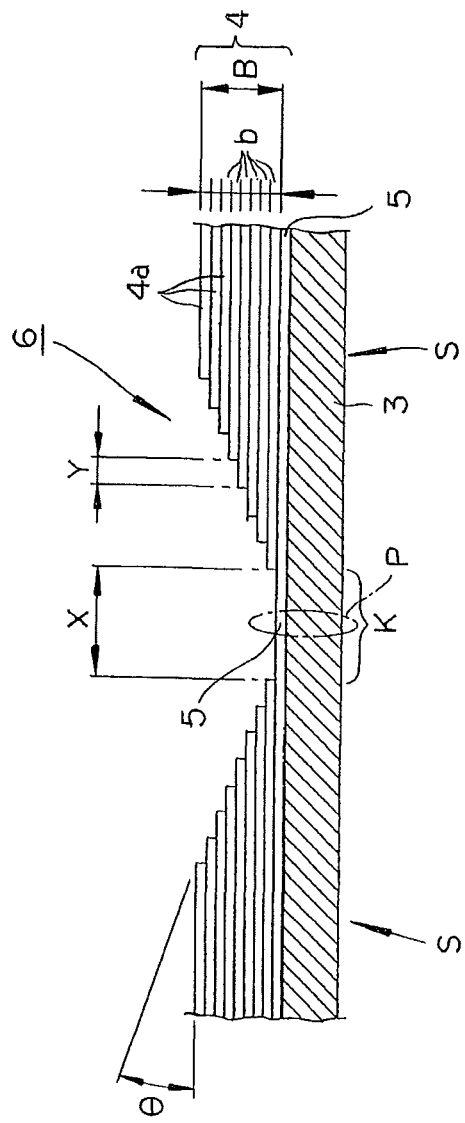
FIG. 6A is a somewhat schematic cross-sectional view of the stent taken along the section line 6-6 of FIG. 5.
Figure 6B:
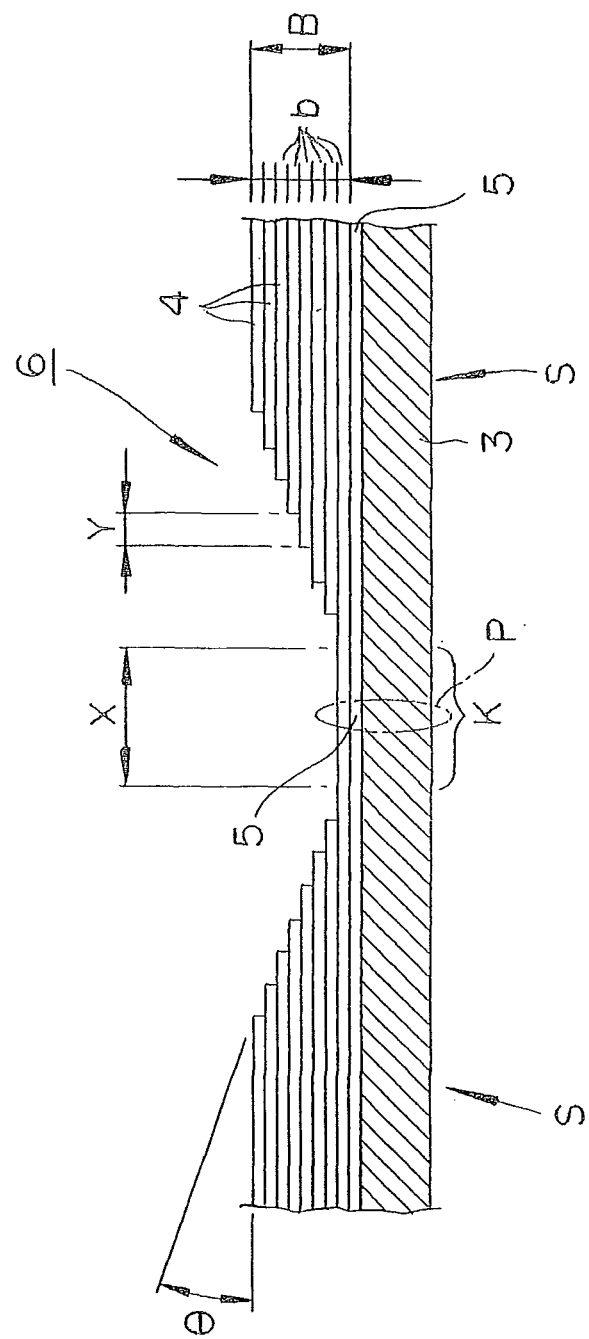
FIG. 6B is a somewhat schematic cross-sectional view of another stent taken along the section line 6-6 of FIG. 5.

Since the spray method, ink jet method and nozzle jet method are basically different only in the process of applying drug to the outside surface of the stent body 2 while the configuration of the drug coat layer 4 to be formed is similar, the following description of an example of forming the coat layer 4 will be based on a nozzle injection method FIGS. 5, 6A and 6B illustrate an example of a drug coat layer 4 on the outside surface of the stent body 2 described hereinabove. In the present embodiment, a lamination method involving spraying and applying coating liquid a large number of times along the strut 3 is used to form the drug coat layer 4 such that the thickness B of the coat layer 4 gradually decreases toward a bent portion K. Then, preferably a primer coat layer 5 is provided between the stent body 2 and the drug coat layer 4. Since the primer coat layer 5 is configured from a material having an adhesive property to polymer which configures a drug coat layer hereinafter described, the bonding between the stent body 2 and the drug is quite good. Consequently, the stent exhibits relatively low exfoliation characteristics.

In the drug coat layer 4 of the present embodiment, the thickness B of the linear portion S of the stent body 2 which is formed from a linear portion or a curved portion is substantially uniform as shown in FIG. 5, while the thickness B from the linear portion S to the bent portion K gradually decreases in a drug coat layer thickness reducing portion, and a gradually decreasing portion 6 is formed such that, at and in the proximity of the bent point P (inflection point), it has no coat layer (no-drug coat layer) with no drug coat as shown in FIG. 6A, or has a very thin drug coat layer (thin drug coat region) as shown in FIG. 6B. In the case of the thin drug coat region, the drug coat layer thickness is less than the thickness of the drug coat layer in all other regions of the outer surface of the stent body other than the thin drug coat regions.

In particular, when a nozzle hereinafter described is moved along a predetermined pattern of the stent body 2 and forms or applies a drug coat layer 4 of the predetermined thickness B using a lamination method of discharging drug to the surface of the stent body 2 to form a plurality of thin film coat layers 4a of a small thickness b, if the coating region of each thin film coat layer 4a is adjusted as the nozzle approaches a bent point P and the proximity of the bent point P and the layer number of the thin film coat layers 4a is reduced stepwise, then the thickness B of the drug coat layer can be gradually decreased readily. Thus, a valley-shaped gradually decreasing portion 6 centered at the bent point P and the proximity of the bent point P is formed. The formation of the thin film coat layer 4a is hereinafter described in detail.

In case the thickness B of the drug coat layer 4 is gradually decreased toward the bent portion K and the proximity of the bent portion K in this manner, then when the stent 1 is to be expanded in a radial direction, even if the start point at which the stent body 2 begins to its deformation is shifted a little from the bent point P of the bent portion K, since the thickness of the drug coat layer 4 which exists at the start point of the deformation and in the proximity of the start point is relatively small, the occurrence of strain or stress concentration on the drug coat layer 4 decreases significantly.

In particular, although the position of the bent point P on the stent body 2 geometrically is a so-called inflection point at the bent portion K, when actually a balloon or the like is used so that expanding force is caused to act from the inside of the stent to expand the stent 1 in a radial direction, the start point at which deformation of the bent portion K of the stent body 2 occurs is not always an inflection point but varies depending upon the acting direction of the expanding force applied to the struts 3 and cannot be specified unambiguously. By forming the gradually decreasing portion 6 of the drug coat layer 4 so that the thickness B of the drug coat layer 4 is gradually decreased toward the bent portion K and the proximity of the bent portion K, even if the position of the bent point P of the stent body 2 is shifted a little, the drug coat layer 4 deforms following the stent body 2, and the strain or the stress concentration which occurs on the drug coat layer 4 is very small. And because the application amount of the drug is relatively small at this portion, also the drug itself is likely to follow up the deformation of the stent body 2. As a result, both of them together improve the effect of preventing coming off of the drug significantly.

Since the bent point P is not specified clearly in such a manner as described above, in FIG. 5, it is indicated by a broken line as a region in which the bent point P may possibly exist.

When a particular example of the gradually decreasing portion 6 is shown in FIG. 6A which indicates the bent portion K in a straight configuration, preferably the thickness b of one thin film coat layer 4a is 1 μm to 5 μm; the layer number of the thin film coat layers 4a is 1 to 50; the length X of the bent portion K is 50 μm to 1000 μm; and the length Y between end portions of upper and lower thin film coat layers 4a (however, the lengths between the end portions are sometimes not equal) is 1 μm to 1,000 μm. The inclination angle θ of the gradually decreasing portion 6 is smaller than 90 degrees, preferably 1 to 60 degrees, more preferably 1 to 45 degrees. In the case where the inclination angle θ is smaller than 1 degree, the effect of preventing coming off of the drug is exhibited over a wide range, while there is the possibility that the drug amount to be coated (i.e., the drug amount actually coated on the stent) may decrease, which is not preferable. On the contrary, where the inclination angle θ exceeds 60 degrees, there is the possibility that the effect of preventing coming off of the drug may be lowered and this is not preferable. The gradually decreasing portion 6 whose inclination angle θ is 1 to 45 degrees can be produced readily by a lamination method described below.

The example described above involves a case in which a portion of the strut constitutes a no-coat layer at which the drug coat layer 4 is not formed. This no-coat layer can extend over a range or length of 50 μm to 1000 μm, centered at the bent point P. This arrangement with the no-coat layer at a position at which concentration of the strain is most likely to occur, helps to ensure that the stent has a relatively high drug coming-off suppression ability. Thus, even if a situation occurs in which the stent must be expanded by a great amount at the indwelled position of the stent, this situation can be readily addressed without the possibility of the same adverse results as would be the case in the absence of the no-coat later. The stent thus exhibits relatively easy handling, and is relatively easy and reliable in procedure and good in convenience in use.

The stent disclosed here is not necessarily limited only to a no-coat layer, and the bent portion K may have one to several thin film coat layers 4a.

The drug coat layer 4 is configured from a mixture of a drug and a polymer. This mixture is preferably configured as a mixture of a drug and a biodegradable polymer. When polymer which covers and protects the drug is biodegraded after the stent is indwelled in an organism, the drug is released and restenosis at the stent indwelled region is prevented with relative certainty. As the biodegradable polymer, it is preferable to use one of polylactic acid, polyglycolic acid, lactic acid-glycolic acid copolymer and lactic acid-ε-caprolactone copolymer.

The mixture rates of the drug and the polymer of the thin film coat layers 4a of the drug coat layer 4 may be equal to each other or may be different from each other. For example, the ratio of the drug to the polymer may increase gradually from the lowermost layer toward an upper layer of the thin film coat layers 4a which contacts with the primer coat layer 5.

Figure 7:
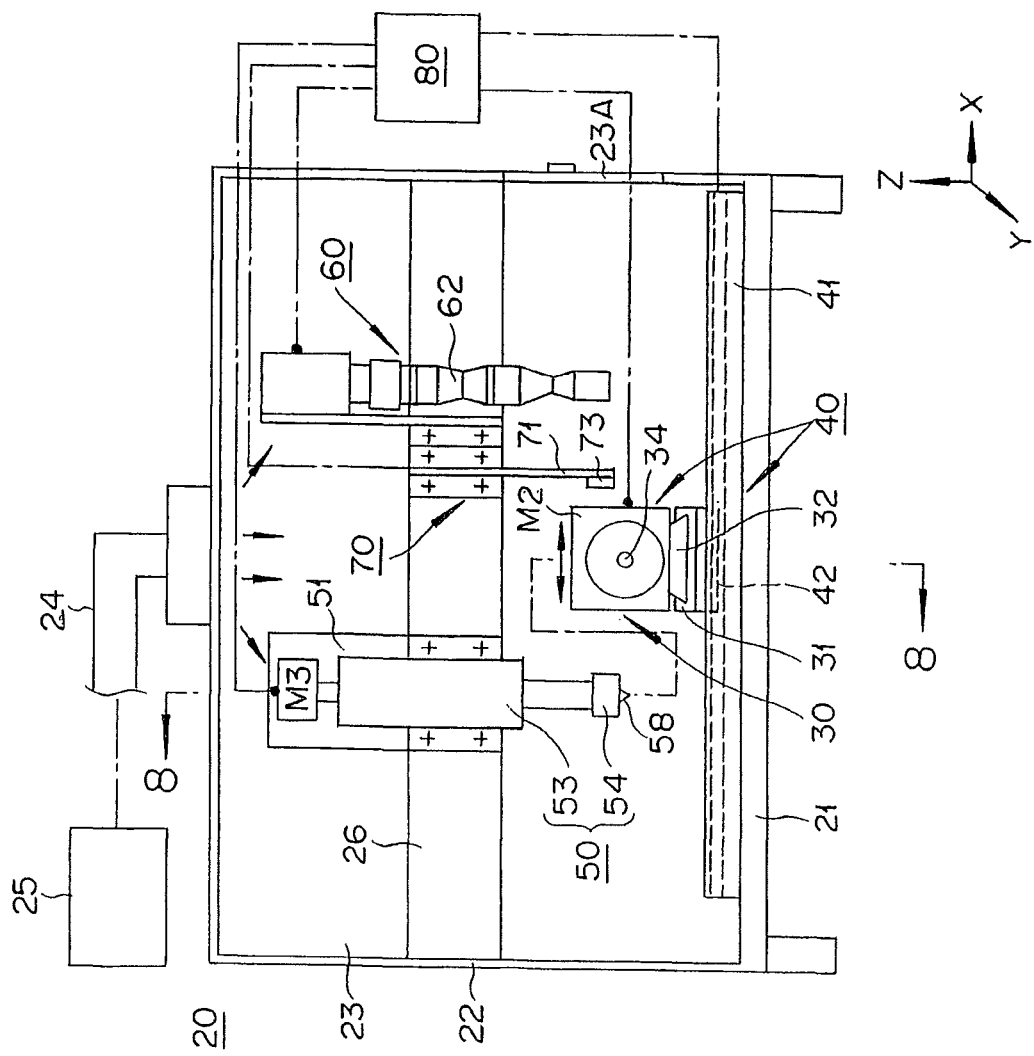
FIG. 7 is a somewhat schematic front view of a coating apparatus.
Figure 8:
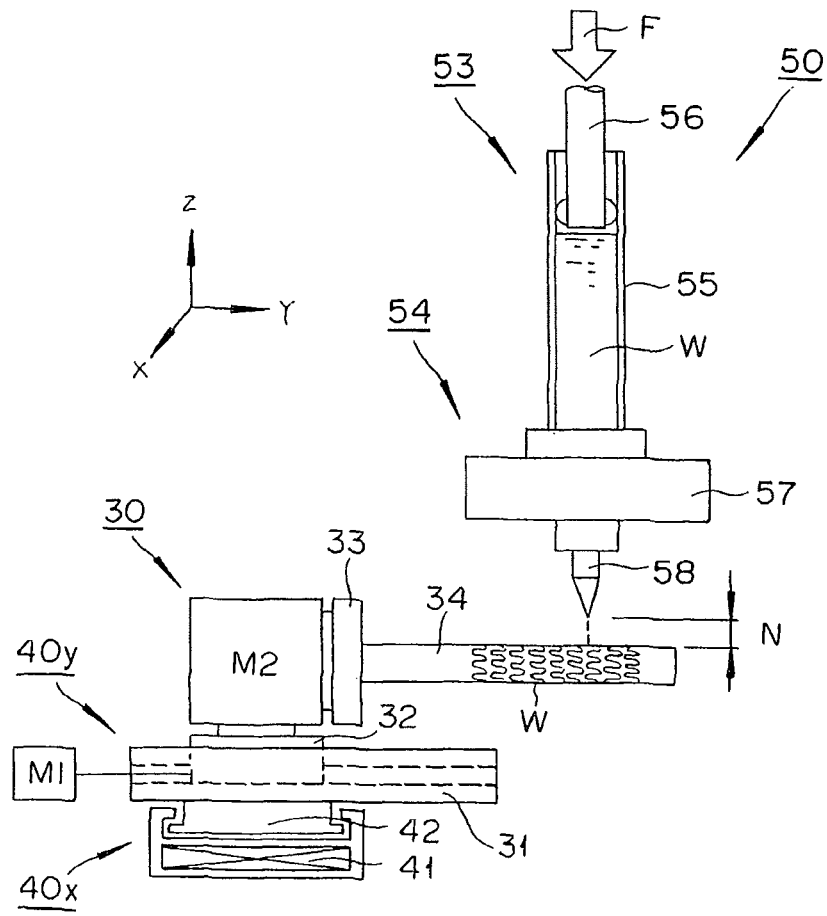
FIG. 8 is a somewhat schematic cross-sectional view taken along the section line 8-8 of FIG. 7.

FIGS. 7 and 8 illustrate a coating apparatus disclosed here by way of example to form the thin film coat layer 4a on the struts of the stent using a lamination method. The coating apparatus 20 includes a frame 22 provided upright on a base 21 and covered with a transparent synthetic resin plate from the outer face thereof to form a chamber 23 having air tightness in the inside thereof. A duct 24 is provided contiguously to a top portion of the chamber 23 so that air whose temperature and humidity is controlled is supplied from an air conditioner 25 to place the inside of the chamber in a state of a constant temperature and a constant humidity to thereby constantly maintain the drying solidifying condition when coating material W hereinafter described is applied to the stent body 2.

At a lower portion in the chamber 23, a holder 30 for holding the stent body 2 and moving means 40 for moving the holder 30 are provided, and at a middle portion in the chamber 23, an application head 50 for applying coating material W to the strut 3 of the stent body 2, first position information acquisition means 60 for acquiring position information in the X-Y directions on a Cartesian coordinate system on the surface of the stent body 2, that is, on the surface of the strut 3, and second position information acquisition means 70 for acquiring position information in the Z direction on the Cartesian coordinate system are provided on a support frame 26 attached to the frame 22.

A control section 80 is external of the chamber 23 and controls the holder 30, the moving means 40, the application head 50, and the position information acquisition means 60 and 70.

As shown in FIG. 8, a mandrel 34 of the holder 30 is chucked at a proximal end thereof by a chucking section 33 connected to a motor M2 which can rotate bidirectionally. The stent body 2 is mounted on the outer periphery of the mandrel 34 and is removable from the mandrel 34.

The motor M2 is placed on a slide section 32, and the slide section 32 is provided for movement (in the Y direction) on a base plate 31. The base plate 31 is placed on a movable table 42 which is moved (in the X direction) along a traveling rail 41 which is a driving source of the so-called linear motor type. Consequently, the holder 30 can move the stent body 2 in the X direction and the Y direction by forward and backward rotation.

Figure 9:
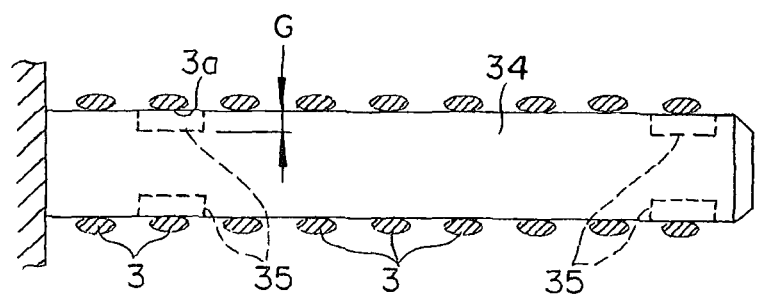
FIG. 9 is a cross-sectional view of a mandrel part of the coating apparatus.

Although the outer diameter of the mandrel 34 preferably is substantially equal to or a little greater than the inner diameter of the stent body 2, as the mandrel 34, mandrels which can be exchanged in accordance with the inner diameter of the stent body 2 and have several outer diameters are prepared. Each of the mandrels is coated with black paint so that it may absorb light thereby to raise the contrast ratio between the strut 3 of the mounted stent body 2 and the gap portion O. Further, the mandrel 34 has recessed portions 35 formed on an outer circumferential face thereof as shown in FIG. 9 so that, when the stent body 2 is mounted on the mandrel 34, a gap G is produced between the outer circumferential face of the mandrel 34 and a lower face (inner surface) 3a of the strut 3 of the stent body 2. Consequently, when the coating material W is applied to the strut 3, the coating material W is prevented from coming round to a place between the surface of the mandrel 34 and the inner side surface of the stent body 2 thereby to achieve formation of a uniform coating layer and convenience of the work.

As shown in FIGS. 7 and 8, the application head 50 has a dispenser 53 and a nozzle section 54. The dispenser 23 is mounted on a bracket 51 which is attached to the support frame 26 through a vertical table, which is moved in the Z direction by a screw feed mechanism or the like which is driven by the motor M3 and which gradually discharges the coating material W reserved in the inside thereof. The nozzle section 54 discharges the coating material W As shown in FIG. 8, the dispenser 53 has a cylinder portion 55 which serves as a syringe operating mechanism and in which coating material W is reserved, a piston portion 56 provided for sliding movement in the cylinder portion 55, and a driving section such as a motor or a hydraulic mechanism for pressing the piston portion 56 by a predetermined force F.

The nozzle section 54 is configured from an attaching member 57 provided at a lower end of the cylinder portion 55, and a nozzle 58 depending from the attaching member 57, and a flow path (not shown) along which the coating material W flows from the cylinder portion 55 to the nozzle 58 is formed.

The outer diameter of the distal end of the nozzle 58 is 10 μm to 1000 μm, and the inner diameter of the distal end of the nozzle 58 is 1 μm to 500 μm, preferably 5 μm to 250 μm, so that the coating material W having a viscosity hereinafter described may be extruded at a predetermined discharge speed. Where the diameter is smaller than 5 μm, the coating material W does not flow out sufficiently smoothly, and a high pressure is sometimes required for the discharge. On the other hand, where the diameter exceeds 250 μm, there is the possibility that the coating material W may not substantially be able to be smoothly applied on the stent body 2 which is currently used.

The nozzle 58 is preferably polished so as to minimize recesses and projections on its surface as far as possible in order to prevent adhesion of the discharged coating material W thereto, and preferably, for example, stainless steel, carbon steel, nickel, titanium, chromium, glass, aluminum oxide, zirconium oxide, diamond or a complex of them are used.

The dispenser 53 is provided such that it is spaced apart from the struts 3 such that the distance N between the nozzle 58 and the strut 3 may be a predetermined length and the coating material W is continuously extruded without being interrupted toward the surface of the struts 3 from the nozzle 58 and placed on the surface of the struts 3. Where such a continuous extrusion method as just described is used, uniform application of the coating material W to a desired portion of the stent body 2 can be achieved. Further, the coating material W can be discharged quantitatively having high controllability, and the quantitative adjustment of the therapeutic substance can be carried out with a high degree of accuracy and with certainty. Besides, since, in the chamber which is adjusted to a constant temperature and constant humidity state, conditions for drying and solidifying the coating material W are fixed, production of the stent 1 to which the coating material W adheres can be carried out relatively readily and rapidly.

The viscosity of the coating material W discharged from the nozzle 58 is 0.1 cp to 10 cp, preferably 1.0 cp to 4.0 cp. Where the viscosity is higher than the range, a high pressure is required or the coating material W cannot sometimes be discharged from the nozzle 58. Where the viscosity is lower than the range, the coating material W may sometimes overflow from the strut 3, resulting in failure to form a uniform application layer.

The distance N between the nozzle 58 and the strut 3 is 0.1 µm to 200 µm, preferably 1 µm to 100 µm. Where the distance N is greater than the range, a problem may arise in that the coating material W is interrupted. Where the distance N is smaller than the range, another problem may arise in that the coating material W overflows from the strut surface.

FIG. 7 illustrates the first position information acquisition means 60 is an image pickup means attached fixedly in position on the support frame 26 through a bracket. The first position information acquisition means 60 has a camera section 62 and a line sensor section disposed so as to extend in the axial direction of the stent body 2. The first position information acquisition means 60 scans the surface of the stent body 2 in synchronism with rotation of the stent body 2 of the holder 30 to capture an image on the surface of the stent body 2, and transmits the image to the control section 80. As described above, since the mandrel 34 is colored black (e.g., painted with a black paint) so as to raise the contrast ratio between the strut 3 of the mounted stent body 2 and the gap portion O and absorbs light, an obtained image of the stent surface is high in luminance of the strut 3 but low in luminance of the gap portion O. Therefore, the control section 80 can binarize the obtained surface image of the stent body 2 with a suitable luminance to fractionate the surface image into the strut 3 and the gap portion O to obtain coordinates of the strut 3, that is, position information of the strut 3 in the X-Y directions. Further, the control section 80 calculates coordinates of a trajectory which passes the center of the strut 3 based on the obtained position information in the X-Y directions (X-Y coordinates of the strut 3), and the obtained data of the center trajectory are stored into a memory of the control section 80. Upon application of the coating material W, it is essential that the application is carried out without being derailed from the struts 3, and also to this end, it is very significant to specify the center of the struts 3.

The second position information acquisition means 70 is a displacement measurement means in the Z direction attached fixedly in position to a lower end of a bracket 71 attached to the support frame 26, and is configured from a laser displacement sensor 73 called vertical sensor for measuring a displacement of the struts 3 in the Z direction.

The surface of the strut 3 strictly is not smooth but has recesses and projections, and in order to quantitatively accurately apply the coating material W to the strut having such recesses and projections, a predetermined amount of coating material W must be applied so that the distal end of the nozzle 58 moves strictly in parallel to the surface of the strut 3. Accordingly, the laser displacement sensor 73 starts acquisition from position information of the strut 3 at a predetermined position of the stent body 2, for example, at an application start point, scans the stent body 2 along a trajectory passing the center of the strut 3 while rotating the stent body 2 forwardly and backwardly, and collects displacement data of the overall stent body 2 in the Z direction. The acquired displacement data is stored into the memory of the control section 80.

The control section 80 has a processor, a monitor, a keyboard and so forth, and from the position information thereof, carries out setting of an application method for applying the coating material W and determination of an application route along which the application head 50 is to apply the coating material W to the strut 3 of the stent body 2. The control section 80 further controls, for example, rotation of the mandrel 34 of the holder 30, movement of the moving means 40, the discharge amount of the coating material W to be discharged from the application head 50, and scanning of the image pickup means or the vertical sensor.

The application method signifies an application route in the case where the application is to be carried out along the strut 3. Although the application route preferably is a route along which the coating material W can be applied to the overall strut 3 continuously without an interval in which overlapping application is carried out, in the case of the stent 1 in which the struts 3 cross with each other in a complicated manner, it is sometimes difficult to set a route which does not include an interval of such overlapping application. In such an instance, an interval in which overlapping application is to be carried out, or an interval across which the application point jumps from a certain point to another point on the strut 3 is provided. By partly providing an interval in which overlapping application is to be carried out or an interval in which the application point jumps in this manner, the application route can be shortened. Further, when the moving speed within an overlapping interval (interval which is passed a plural number of times) is set higher than the moving speed within an interval which is passed only once, the drug can be applied relatively uniformly to a desired portion of the stent body 2, and the effect of reducing the restenosis rate can be exhibited sufficiently in the case of PTCA or the like. Particularly in the case where the coating material W is applied to form the gradually decreasing portion 6 whose thickness gradually decreases toward the bent portion K as in the present embodiment, it is preferable to move the nozzle 58 from one side of the strut 3 of the bent portion K toward the other side opposing the one side, while skipping over the bent portion. That is, as the nozzle 58 is moved along the strut 3 and approaches the bent portion, the nozzle 58 is moved in such a way that the nozzle 58, and the application of the coating material, skips over the bent portion. By such movement, the gradually decreasing portion 6 can be formed relatively rapidly.

Upon determination of an application route, it is preferable to implement various additional measures such as those described below.

Where the coating material W is applied to the strut 3 of the stent body 2, at the linear portion S of the strut 3, it is preferable to set a trajectory which passes the center of the strut 3 as the application route. However, at the bent portion K of the strut 3, it is preferable to set a trajectory which passes a position shifted by a predetermined distance in a widthwise direction of the strut 3 as the application route. The coating material W is liquid and exists in a state in which it swells upwardly on the surface of the strut 3 due to the surface tension of the liquid, and even if it is dried and solidified, it is likely to form a coating layer having an arcuate cross-section. Accordingly, where the coating material W is applied a plural number of times, since it is liable to swell arcuately, it is preferable to set a trajectory which passes a position shifted by a predetermined amount from the coating layer of the strut 3 for the first time as an application route to form a coating layer for the second time, and to set as the application route for the coating layer for the third time a trajectory which passes a position different from the application routes for the first time and the second time.

Upon determination of an application route, it is preferable to use different application routes for the linear portion S and the bent portion K. In the linear portion S, a trajectory which passes the center of the strut 3 may be set as the application route as described above. However, in the bent portion K, if a trajectory which passes the center of the strut 3 in the widthwise direction is set as the application route, then the coating material W discharged from the application head 50 does not follow up the moving trajectory of the application head 50 by an influence of the viscosity of the coating material W, the dropping speed of the coating material W from the nozzle and so forth. Accordingly, it is preferable to set the outer side relative to a line which passes the center of the bent portion K of the strut 3 as the application route.

At a crossing point of the struts 3, it is preferable to set a cross point of the center axial lines of the plural struts 3 or the proximity of the cross point as the application route. At a location at which the struts 3 cross with each other, since also the application routes P therefor cross with each other, if a cross point of the center axial lines of the plural struts 3 or the proximity of the cross point is set as the application route, then also flowing down of the coating material W can generally be prevented favorably.

Figure 10:
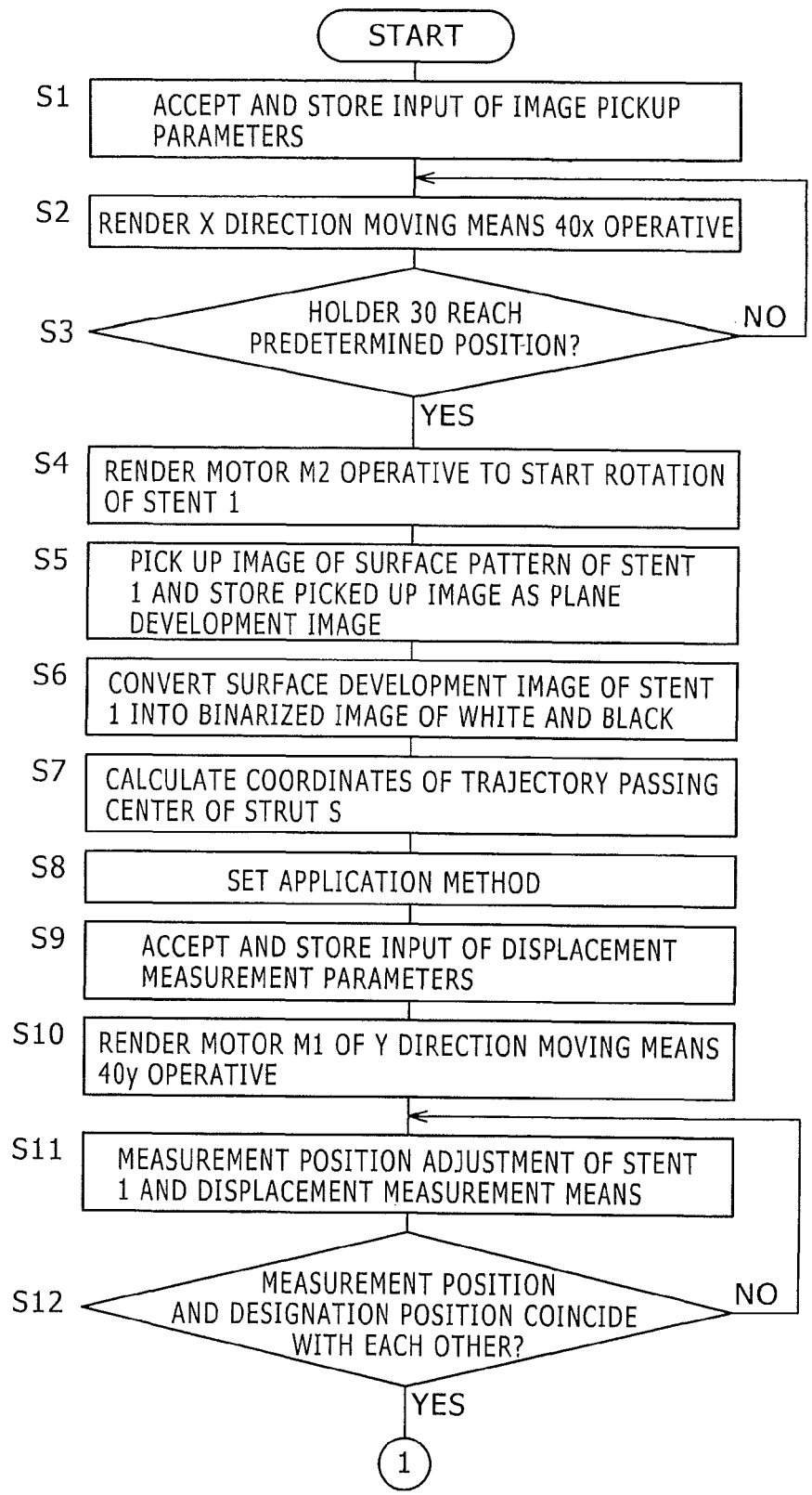
FIG. 10 is a flow chart illustrating a part of the coating process.
Figure 11:
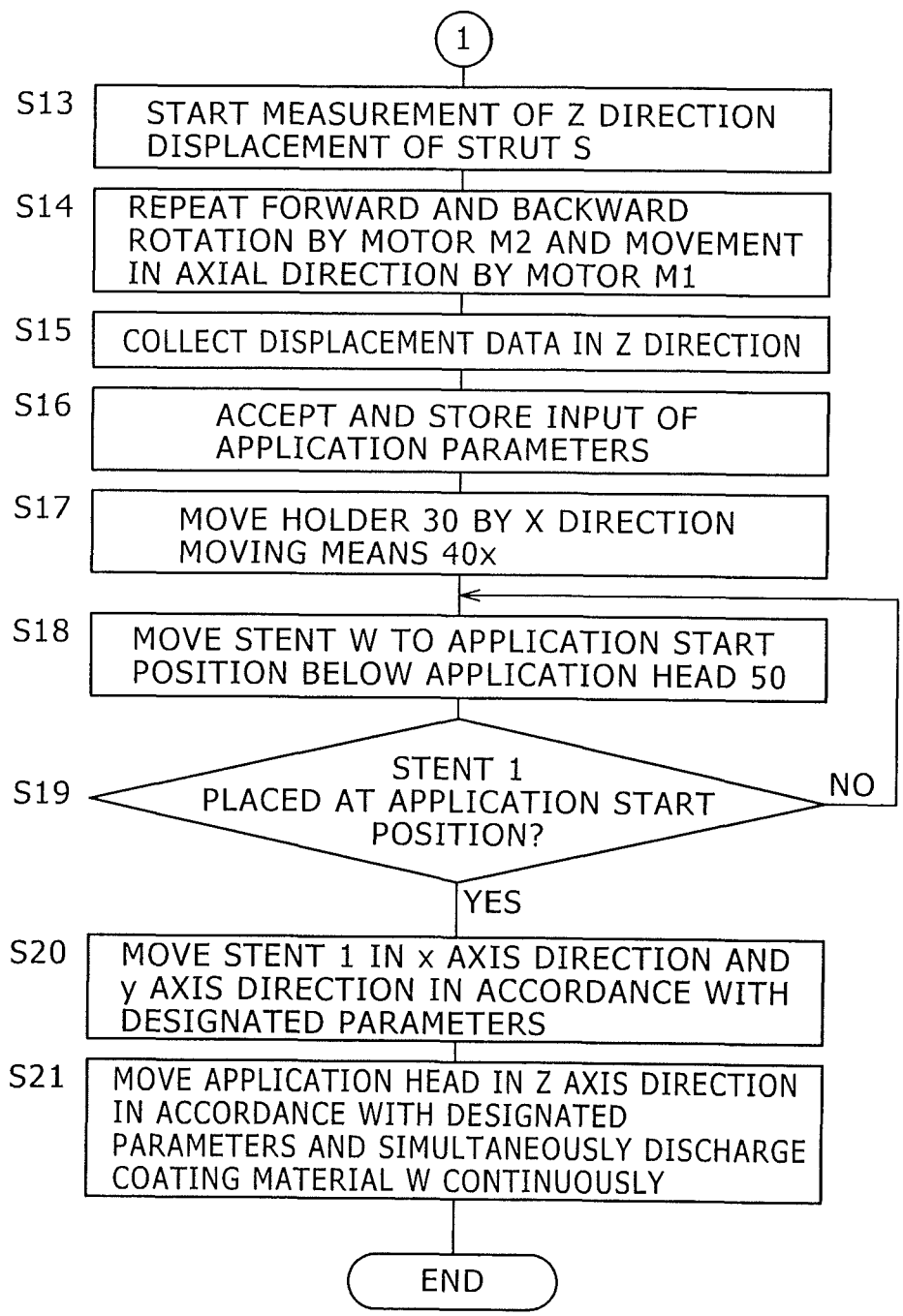
FIG. 11 is a flow chart illustrating a remaining part of the coating process of FIG. 10.

A coating method will now be described by way of example with reference to FIGS. 10 and 11 which depict a flow chart or process routine of the coating process.

Preparation Step

First, before coating is started, the air conditioner 25 is rendered operative to place the inside of the chamber 23 in a constant temperature and constant humidity state. Then, the syringe operating mechanism 53 formed by the combination of the nozzle section 54 having the nozzle 58 of an inner diameter corresponding to the width of the strut 3 or the coating material W, the cylinder portion 55 in which the coating material W is injected and so forth is set or secured to the support frame 26.

The stent body 2 is attached, after mounted on the mandrel 34, to the chucking section 33 of the holder 30 positioned at a standby position and set such that the application start point of the strut 3 is positioned on a recessed portion 35 of the mandrel 34. It is to be noted that the standby position is a position in the proximity of an entrance portion 23A of the chamber 23 in the case where the moving means 40 is provided at a lower portion of the chamber 23, as shown in FIG. 7.

Image Pickup Step

The control section 80 accepts an input of image pickup parameters and stores the inputted image pickup parameters into the storage device (S1). The image pickup parameters are inputted, for example, from a keyboard by an operator. The image pickup parameters include a speed of rotation of the mandrel 34, an image pickup line number, an image pickup line width, and an image pickup operation speed.

The control section 80 issues an instruction to start image pickup after the inputted image pickup parameters are stored. Simultaneously, the control section 80 renders the X direction moving means 40x operative (S2). Consequently, the holder 30 moves from the standby position to a position below the first position information acquisition means 60 along the traveling rail 41. The control section 80 confirms that the holder 30 comes to or has reached the predetermined position (S3), and when the holder 30 reaches the predetermined position, the control section 80 renders the motor M2 of the holder 30 operative to start rotation of the stent 1 (S4).

The line sensor of the first position information acquisition means 60 starts image pickup in accordance with an image pickup starting instruction and scans the surface of the stent body 2 to pick up an image of the surface pattern (S5). The picked-up image is stored as a plane developed image into a storage device (for example, a memory, a hard disk or the like) in the control section 80. The image may be outputted to a monitor so that it can be confirmed by visual observation.

Since, in the surface image of the stent body 2, the luminance of the strut 3 is high and the luminance of the gap portion O is low, the control section 80 converts the surface image into a binarized image of white and black with reference to a certain luminance (S6), and calculates coordinates of a trajectory which passes the center of the strut 3 by a reduction process of the width of the strut 3 (S7).

Setting Step of an Application Method

Deciding from the acquired surface image of the stent body 2 and taking whether an interval within which overlapping application is to be carried out and an interval across which the application point is to jump and the position of such intervals into consideration, an application route is set such that, while the application is performed for a desired surface portion of the strut 3, those intervals for overlapping application and those intervals for jumping are reduced in number or length as far as possible or as much as possible (S8).

Displacement Measurement Step in the Z Direction

Further, the control section 80 accepts and stores an input of displacement measurement parameters of the second position information acquisition means 70 which serves as the displacement measurement means in the Z direction (S9). Also these displacement measurement parameters are inputted by the operator. The displacement measurement parameters include a measurement start position, a direction of the measurement, a direction at a branch point, a measurement speed and a measurement interval.

The control section 80 renders operative a motor M1 of the Y direction moving means 40y after the storage of the displacement measurement parameter (S10). If necessary, while the stent body 2 is observed by means of a video camera and a monitor, the measurement positions of both the stent body 2 and the displacement measurement means are adjusted so that the measurement position of the displacement measurement means and the designation position on the trajectory coincide with each other (S11).

After the measurement position and the designation position are brought into coincidence with each other by the adjustment (it is to be noted that such coincidence is inputted to the control section 80 by the operator) (S12, Yes)), the control section 80 issues an instruction to start measurement of the displacement in the Z direction of the strut 3 to the second position information acquisition means 70 (S13). The control section 80 causes forward and backward rotation by the motor M2 and movement in the axial direction by the motor M1 to be repeated. Consequently, the stent body 2 repeats the rotation and the axial direction movement (S14).

Consequently, since the second position information acquisition means 70 moves along a trajectory which passes the center of the strut 3, the control section 80 collects displacement data in the Z direction (S15). The displacement data are stored into the storage device of the control section 80 together with the coordinates of the center trajectory.

Application Step

The control section 80 accepts and stores an input of application parameters (S16). Also the application parameters are an input by the operator. The application parameters include an application start position, a direction of the application, a direction at a cross point, setting of a trajectory adjustment interval, an adjustment amount of the trajectory, an application speed, a discharge speed of the coating material W, a height of the application head, an application time number (number of layers) and selection of an application head.

The control section 80 issues an instruction to start application after the storage of the application parameters. Simultaneously, the control section 80 issues an instruction to move the holder 30 by means of the X direction moving means 40x (S17). Consequently, the stent body 2 is moved to the application start position below the application head 50 (S18). After the stent body 2 reaches the application start position below the application head 50 (S19: Yes), the control section 80 issues an instruction to carry out forward and backward rotation by the motor M2 and movement in the axial direction by the motor M1 so that the stent body 2 is moved in the x axis direction and the y axis direction in accordance with the designated parameters by forward and backward rotation by the motor M2 and movement in an axial direction by the motor M1 (S20). Simultaneously, the control section 80 causes the application head 50 to move in the Z axis direction by operation of the motor M3 in accordance with the designated parameters (S21). At this time, the coating material W is discharged continuously from the application head 50. Consequently, while the application head 50 moves along the application route determined in advance, application of the coating material W is carried out.

During the application, since the space between the distal end of the nozzle 58 and the stent body 2 is in a state in which it is filled with the coating material W, the coating material W is discharged by a fixed amount, and also the amount of the drug on the stent body 2 is set to the predetermined value with relative certainty. Besides, a web or a bridge does not appear between the struts 3, and the drug coat layer 4 can be formed with a very high degree of accuracy.

After the coating is completed, the holder 30 is moved to the standby position by the X direction moving means 40x, the mandrel 34 can be taken out from the holder 30 to the outside of the chamber 23 and then the stent body 2 on which the drug coat layer 4 is formed can be removed from the mandrel 34.

The present invention is not limited only to the embodiment described above, but can be modified in various ways by a person skilled in the art within the technical scope of the present invention. For example, although the embodiment described above discloses the gradually decreasing portion 6 along which the thickness B of the drug coat layer linearly varies toward the bent portion K or the proximity of the bent portion K, the shape of the gradually decreasing portion 6 of the present invention is not limited to this. What is desirable is that the thickness B of the drug coat layer is reduced at the bent portion K and in the proximity of the bent portion K, relative to the adjoining portions, and so the gradually decreasing portion 6 may have various shapes such as an arcuate shape.

Further, the coating material W need not be only one kind, as a plurality of kinds of materials may be used. Where a plurality of coating materials W are to be applied, a plurality of syringes, nozzles and syringe operating mechanisms are prepared and successively changed over to carry out coating. Such successive changeover of the syringe operating mechanisms and so forth can be controlled by the control section 80. Here, the different coating materials W relate to a case wherein different polymers are used or a single polymer is used but by different amounts, or different drugs are used or a single drug is used but by different amounts, or else different solvents are used. When a plurality of kinds of coating materials are used in this manner, the efficacy is also complex, which is very advantageous in that physical or spiritual stress to the patient is reduced and so forth.

The method of forming the drug coat layer 4 is also not limited only to that of the embodiment described above, but, for example, a spray or an ink jet may be used.

Further, although the embodiment described above is a wavy stent having a predetermined pattern, the stent is not limited to such a stent as just described, but may have any other pattern possessing a bent portion K.

The stent disclosed here can be utilized as a stent which significantly reduces the restenosis rate after percutaneous transluminal coronary angioplasty (PTCA).

The detailed description above describes features and aspects of an embodiment of a stent and a method for fabricating a stent. The invention is not limited, however, to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A stent radially inwardly contractible to permit placement of the stent in a body lumen and radially outwardly expandable after placement in the body lumen to secure an opening in the body lumen, the stent comprising:
   a cylindrical stent body comprised of a plurality of annular wavy bodies each comprised of a plurality of bent portions and a plurality of connecting portions, with each connecting portion connecting pairs of the bent portions, the bent portions each possessing an Inflection point, the bent portions being subjected to deformation when the stent is contracted and expanded;
   the plurality of annular wavy bodies being axially arranged, with axially adjacent ones of the annular bodies connected by a joint portion; and
   a drug coat layer on an outer surface of said annular wavy bodies;
   wherein the drug coat layer includes a plurality of drug coat layer thickness reducing regions on the outer surface of the wavy bodies defining a thickness that gradually decreases in a predetermined stepwise manner toward the bent portion, the drug coat layer thickness reducing regions being located at parts of the wavy bodies on opposite sides of the inflection points of the bent portions.

2. The stent according to claim 1, further comprising a primer coat, different from the drug coat layer, interposed between an outer surface of the stent body and the drug coat layer so that the primer coat contacts both the outer surface of the stent body and the drug coat layer.

3. The stent according to claim 1, wherein the inflection point of each bent portion is devoid of the drug coating layer.

4. The stent according to claim 1, wherein the drug coat layer is comprised of a plurality of layers of the drug coat.

5. The stent according to claim 1, wherein the connecting portions of the plurality of annular wavy bodies define linear portions where the drug coat layer has a uniform thickness.

6. The stent according to claim 1, wherein the plurality of drug coat layer thickness reducing regions define an inclination angle less than ninety degrees.

7. The stent according to claim 1, wherein the plurality of drug coat layer thickness reducing regions define an inclination angle between one and sixty degrees.

8. The stent according to claim 1, wherein the plurality of drug coat layer thickness reducing regions define an inclination angle between one and forty five degrees.

9. The stent according to claim 1, wherein the drug coat layer comprises a mixture of a drug and a polymer.

* * * * *